United States Patent [19]

Hilgers et al.

[11] Patent Number: 4,929,727

[45] Date of Patent: May 29, 1990

[54] IMPROVED PROCESS FOR PRECIPITATING CYTOSINE FROM ALKALINE SOLUTIONS WITH SULFURIC ACID

[75] Inventors: Georg Hilgers, Ingelheim am Rhein; Joachim Hess, Bingen, both of Fed. Rep. of Germany

[73] Assignee: Boehringer Ingelheim KG, Ingelheim am Rhein, Fed. Rep. of Germany

[21] Appl. No.: 398,864

[22] Filed: Aug. 25, 1989

[30] Foreign Application Priority Data

Aug. 27, 1988 [DE] Fed. Rep. of Germany ....... 3829100

[51] Int. Cl.$^5$ ................... C07D 239/34; C07D 239/42

[52] U.S. Cl. .................................................. 544/317
[58] Field of Search ........................................ 544/317

[56] References Cited

U.S. PATENT DOCUMENTS 2,892,840  6/1959  Tarsio et al. ........................ 544/317

Primary Examiner—John M. Ford
Attorney, Agent, or Firm—D. E. Frankhouser; M-E. M. Timbers; A. R. Stempel

[57] ABSTRACT

The invention relates to an improved process for precipitating cytosine from an aqueous solution of an alkali or alkaline earth metal salt of cytosine using sulfuric acid.

9 Claims, No Drawings

IMPROVED PROCESS FOR PRECIPITATING CYTOSINE FROM ALKALINE SOLUTIONS WITH SULFURIC ACID

This invention relates to an improved process for precipitating cytosine (I).

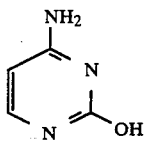

Cytosine (I) is of major importance as the central intermediate product in the preparation of pharmacologically active derivatives. Thus, for example, the arabinoside of cytosine can be used effectively for treating leukemia.

Whereas various methods are known from synthesizing the pyrimidine structure on which cytosine (I) is based [D. T. Hurst, The Chemistry and Biochemistry of Pyrimidines, Purines and Pteridine, John Wiley and Sons Chichester 1980], basically the only method known of preparing cytosine (I) directly, which does not require the pyrimidine basic structure to be synthesized beforehand, is the base-induced reaction of urea with 3-ethoxyacrylonitriles [U.S. Pat. No. 2,892,840; P. J. Tarsio and L. Nicholl, J. Org. Chem. 22 (1957) 192] or of urea with 1-cyano-2,2-diethoxyethane [A. Bendich, H. Getler and G. B. Brown, J. Biol. Chem. 177 (1949) 565].

In the methods cited, urea (IV) is first of all reacted in the presence of sodium n-butoxide under reflux conditions with 3-ethoxyacrylonitrile or 1-cyano-2,2-diethoxyethane to obtain an intermediate product, which is not further characterized, and which is treated with sulfuric acid in a subsequent reaction step. A disadvantage of the reactions used in these processes, some of which are complex, is that it is impossible to obtain the free cytosine base (I); only the addition salts thereof with sulfuric acid, namely the sulfate or hemisulfate, are isolated, and the cytosine (I) can only be obtained from them with high losses of yield.

The cytosine (I) isolated after dissolving of cytosine sulfate or hemisulfate by the addition of ammonia is an addition highly contaminated with, inter alia, cytosine sulfate, which has similar properties of solubility.

It is only possible to separate the cytosine (I) from these impurities completely by accepting high losses of yield of cytosine (I) and using large quantities of solvent.

Other disadvantages of this process are the necessity to use a very large quantity of sulfuric acid, in relation to the size of the reaction mixture, this sulfuric acid being needed to produce the cytosine salts according to the prior art. The cytosine salts then also have to be reacted in turn with large quantities of aqueous ammonia solution in a further reaction step in order to liberate the cytosine base (I), resulting in additional problems of disposal for the quantities of salts produced.

The cytosine sulfate contained as an impurity can only be removed by adding, again, relatively large quantities of ethanol.

EP No. 82 339 and DE-OS No. 34 34 142 disclose processes based on the reaction of urea (IV) with 3-alkoxyacrylonitriles and/or 3,3-dialkoxypropionitriles, which make it possible to isolate cytosine from the reaction mixture by neutralization with formic acid, acetic acid, hydrochloric acid or phosphoric acid, without requiring isolation of an intermediate product or a cytosine salt. However, EP No. 82 339 and DE-OS No. 34 34 142 also imply that sulfuric acid is not suitable for neutralization in order to isolate the free cytosine (I) in the processes disclosed in these publications.

The process disclosed in EP No. 82 339 additionally yields cytosine (I) only in poor yields, whereas the process disclosed in DE-OS No. 34 34 142 is highly complex and requires the reaction mixture to be evaporated twice to dryness.

The aim of the present invention is to provide a process which can be used to produce cytosine (I) in a onepot process avoiding the use of large quantities of solvents or neutralizing agents, whilst giving a high yield and a high degree of purity.

Starting from the reaction of 3-alkoxyacrylonitriles of general formula II and/or 3,3-alkoxypropionitriles of general formula III with urea (IV) in the presence of alkali or alkaline earth metal alkoxides or hydroxides in accordance with the following reaction plan:

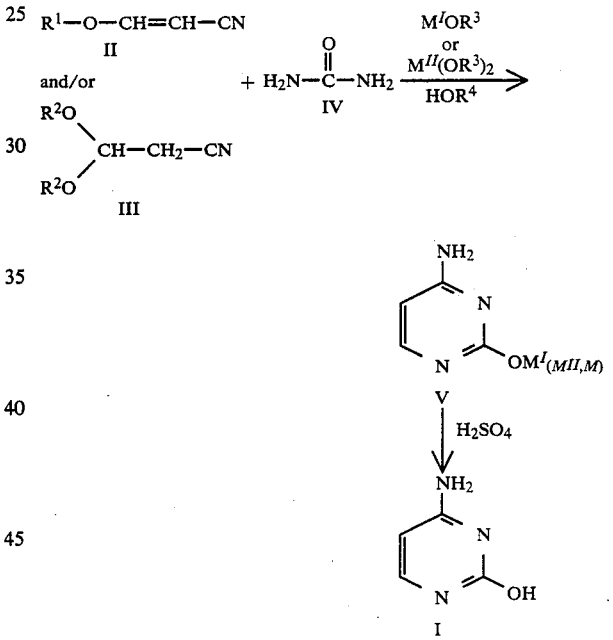

wherein $R^1$ and $R^2$, independently of each other, represent a $C_{1-12}$ straight-chained or branched alkyl or alkenyl group which may optionally be substituted with one or more inert substituents, such as fluorine, methoxy, ethoxy or amino, which may be different from or identical to one another, a mono- or polynuclear $C_{6-10}$ aryl group, in which the aromatic group may be substituted with one or more alkyl groups, alkoxy groups, nitro groups, amino groups and/or one or more halogen atoms, the substituents being identical or different, a $C_{7-14}$ aralkyl group wherein the aromatic group is homo- or polynuclear and bound via an alkylene chain, in which the aromatic group may be substituted with one or more alkyl, alkoxy, nitro or amino groups and/or one or more halogen atoms, which may be identical or different, a $C_{5-9}$ cycloalkyl group bound via an alkylene chain, wherein one or more carbon atoms may be replaced by a heteroatom such as nitrogen, oxygen or sulphur and which may optionally be substituted with one or more of the above-mentioned inert substituents, which may be identical or different;

$R^3$ represents hydrogen, methyl, ethyl, propyl, isopropyl, butyl, isobutyl, tert.-butyl, pentyl, tert.-pentyl (2-methyl-2-butyl), neopentyl, hexyl, isohexyl, cyclohexyl;

$R^4$ represents methyl, ethyl, propyl, isopropyl, butyl, isobutyl, tert.-butyl, pentyl, tert.-pentyl, neopentyl, hexyl, isohexyl, cyclohexyl;

M represents a cation;

$M^I$ represents an alkaline metal cation;

$M^{II}$ represents an alkaline earth metal cation; the corresponding cytosine V alkali or alkaline earth metal salt is obtained.

Preferably:

$R^1$ and $R^2$ independently of each other represent a branched or unbranched $C_{1-4}$ alkyl group such as methyl, ethyl, propyl, isopropyl, butyl, isobutyl, tert.-butyl;

$R^3$ represents methyl, ethyl, propyl, isopropyl, butyl, tert.-butyl, tert.-pentyl (2-methyl-2-butyl);

$R^4$ represents methyl, ethyl, propyl, isopropyl, butyl tert.-butyl, pentyl, tert.-pentyl;

$M_I$ represents Na+, K+.

Particularly preferably, $R^1$ and $R^2$ independently of each other represent methyl, ethyl;

$R^3$ represents methyl, ethyl, isopropyl, tert.-butyl, tert.-pentyl;

$R^4$ represents ethyl, propyl, isopropyl, butyl, tert.-butyl;

$M^I$ represents Na+, K+.

Surprisingly, it has now been found that pure cytosine (I) can be obtained by neutralization or acidification of an aqueous solution of the reaction mixture resulting from this reaction with sulfuric acid. According to the invention, the aqueous basic solution of the above-mentioned alkaline reaction mixture is adjusted to a pH in the range from 2-7, preferably 6-7, at elevated temperature using sulfuric acid. Then the solid constituents are separated from the reaction solution, for example by filtration, and the cytosine obtained on cooling of the filtrate is isolated.

The cytosine (I) prepared by the process according to the invention is not contaminated with cytosine sulfate or cytosine hemisulfate and is obtained in high yields and with a very high degree of purity, which means that the product can be further processed directly—in particular in order to produce pharmaceutical preparations—without any further purification.

The alkaline or alkaline earth metal salt V of the cytosine (I) is prepared—in a manner known per se—by reacting 3-alkoxyacryonitriles or 3,3-dialkoxypropionitriles—preferably 3-methoxyacrylonitrile or 3-ethoxyacrylonitrile—with urea (IV) and a base—preferably an alkali metal alkoxide and particularly preferably sodium tert.-amylate, sodium tert.-butoxide, sodium isopropoxide, sodium ethoxide or sodium methoxide—in a solvent.

The solvents used are polar solvents such as alcohols, preferable $C_{1-6}$ alcohols, and especially ethanol, n-propanol, isopropanol, n-butanol and tert.-butanol.

Sulfuric acid, preferably dilute sulfuric acid and more especially 50% sulfuric acid is used to precipitate the cytosine (I).

However, the cytosine (I) can also be precipitated by first lowering the pH of the reaction solution with an inorganic acid or carboxylic acid and carrying out the actual precipitation of the cytosine (I) with sulfuric acid, the cytosine (I) thus produced also being isolated in a high yield and with a high degree of purity.

The reaction of the urea (IV) with 3-alkoxyacrylonitriles or 3,3-dialkoxyproionitriles—preferably with 3-methoxyacrylonitrile or with 3-ethoxyacrylonitrile or with 3,3-dimethoxypropionitrile—and—preferably the alkali metal alkoxide, is expediently carried out under anhydrous conditions and under an inert gas at a temperature in the range from 70° to 80° C. and preferably at 75° C. Depending on the reactivity of the reactants, however, a higher or lower temperature may also be necessary.

During the reaction it has proved expedient to add the urea (IV) to the solution of the alkali metal alkoxide or alkaline earth metal alkoxide in a polar solvent, preferably an alcohol, this solution being heated to 75° C. under an inert gas, whilst when alcohols are used as the reaction medium the alkoxide residue of the base ($R^3$) need not necessarily be identical to the alkyl residue ($R^4$) of the corresponding alcohol which is used as the solvent.

The 3-alkoxyacrylonitrile or 3,3-dialkoxypropionitrile—preferably 3-methoxyacrylonitrile or 3-ethoxyacrylonitrile or 3,3-dimethoxypropionitrile—optionally in a solution and possibly in the solvent used as reaction medium—is then added, after which the reaction mixture is heated to reflux temperature. When the reaction has ended, the reaction mixture is substantially freed from the solvent, possibly under reduced pressure, until a suspension remains which is still stirrable.

The suspension is then mixed with water and all the reaction constituents with a boiling point of <85° C. are distilled off.

Then, at a temperature in the range from 50° to 80° C., preferably between 70° and 80° C., the pH of the reaction mixture is adjusted to a level in the range from 2-7, preferably 6-7, using sulfuric acid, preferably dilute sulfuric acid and more especially about 50% sulfuric acid, a suspension of activated charcoal in water is added to the solution and the resulting mixture is heated to reflux temperature.

The activated charcoal is subsequently separated from the reaction mixture, which is still at a temperature of about 80° C., using a preheated pressure filter and the filtrate is cooled to 20° C. The cytosine (I) precipitated is isolated and washed with water and dried in vacuo at 60° C. until a constant weight is obtained.

For each mole of 3-alkoxyacrylonitrile—preferably 3-methoxyacrylonitrile or 3-ethoxyacrylonitrile—or 3,3-dialkoxypropionitrile—preferably 3,3-dimethoxypropionitrile—1 to 3, preferably 1 to 2 mol of urea are used and 1 to 3 mol, preferably 1.7 to 2.2 mol of base or alkali metal alkoxide. When aqueous solvents are used it is expedient to increase the quantity of base used accordingly.

The Example which follows is intended to illustrate the invention without being restrictive.

EXAMPLE 9.5 l of isopropanol are combine with 2.085 kg (37.819 mol) of sodium methoxide (content 98%) under an inert gas atmosphere and the mixture is heated to 75° C. Then, with stirring, 2.107 kg (34.380 mol) of urea (content 98%) are added at 75° C. over a period of 20 minutes. After it has all been added a mixture of 2.000 kg (20.181 mol) of 3-ethoxyacrylonitrile (content 98%) is also metered in, with stirring and at 75° C. over a period of 15 minutes. The metering equipment is rinsed out with 1 liter of isopropanol.

The brown reaction mixture is heated for 3 hours to reflux temperature, and the formation of a solid is observed. 9.4 liters of isopropanol are then distilled off. The suspension remaining is combined with 11.5 liters of water within 10 minutes with stirring. The resulting brown solution is heated to reflux temperature (about 85° C.) and 3.0 liters of isopropanol/water mixture are distilled off. The reaction mixture is then allowed to cool to 75° C. and neutralized with 50% sulfuric acid until a pH of 7 is obtained, 2 liters of water are added and the reaction mixture is allowed to cool to 60° C. Subsequently, a dispersion of 0.125 kg of activated charcoal in 0.5 liters of water is added to the mixture which is then heated to reflux temperature with stirring and stirring is then continued for a further 15 minutes. The reaction mixture is then filtered over a pressure filter heated to about 80° C. and the residue is washed with 2 liters of water heated to 80° C. The filtrate is cooled to 20° C. and the product which crystallizes out is suction filtered using a filter lined with a filter cloth.

The residue is washed with water (20° C.) and suction filtered until dry and dried in a drying cupboard under reduced pressure at a temperature of 60° C. until a constant weight is achieved. 1.75 kg (78.1% of theory) of cytosine are obtained as a white amorphous powder.

M.P.: 313°–316° C. decomp. Purity: >99% (HPLC)

What is claimed is:

1. A process for precipitating cytosine from an aqueous solution of

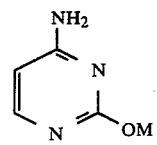

wherein
M is a cation which comprises:
 (a) heating the solution to about 50°–80° C.;
 (b) adjusting the pH of such heated solution with sulphuric acid to about 2–7;
 (c) removing solid constituents from the resulting solution; and
 (d) cooling the remaining solution to about 20° C.; and
 (e) recovering the precipitated cytosine.

2. The process as recited in claim 1 wherein the cation is an alkali metal cation or an alkaline earth metal cation.

3. The process as recited in claim 2 wherein the cation is sodium or potassium.

4. The process as recited in claim 1 wherein the pH is adjusted to 6–7.

5. The process as recited in claim 1 wherein the solution is heated to 70°–80° C.

6. The process as recited in claim 1 wherein the solid constituents are removed by filtration.

7. The process as recited in claim 1 wherein the solid constituents are removed by adding a suspension of activated charcoal in water and then the resulting mixture is heated to reflux temperature.

8. The process as recited in claim 1 which further comprises lowering the pH of the aqueous solution of

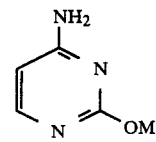

with an organic or inorganic acid prior to heating the solution.

9. The process as recited in claim 1 wherein the sulphuric acid is 50% sulphuric acid.

* * * * *